United States Patent [19]
Mordon et al.

[11] Patent Number: 5,370,119
[45] Date of Patent: Dec. 6, 1994

[54] DEVICE FOR MEASURING THE PH OF A TARGET, METHOD FOR USING SAID DEVICE AND APPLICATIONS THEREOF

[75] Inventors: Serge Mordon, Villeneuve D'Ascq; Vincent Maunoury, Lambersart; Jean-Marie Devoisselle, Montpellier, all of France

[73] Assignee: Institut National de la Sante et de la Recherche Medicale-INSERM, Paris Cedex, France

[21] Appl. No.: 81,276
[22] PCT Filed: Jan. 3, 1992
[86] PCT No.: PCT/FR92/00006
   § 371 Date: Oct. 29, 1993
   § 102(e) Date: Oct. 29, 1993
[87] PCT Pub. No.: WO92/12412
   PCT Pub. Date: Jul. 23, 1992

[30] Foreign Application Priority Data
Jan. 4, 1991 [FR] France ................... 91 00064

[51] Int. Cl.⁵ ............................................. A61B 6/00
[52] U.S. Cl. ......................... 128/654; 128/665; 128/634
[58] Field of Search .................. 128/632–635, 128/637, 664–666, 654; 436/68, 133, 163, 172

[56] References Cited

U.S. PATENT DOCUMENTS

4,768,513  8/1988  Suzuki .
4,973,848 11/1990  Kolobanov et al. .
5,093,266  3/1992  Leader et al. ............. 128/635 X

FOREIGN PATENT DOCUMENTS

2126717  3/1984  United Kingdom .
8404665 12/1984  WIPO .
9010219  9/1990  WIPO .

OTHER PUBLICATIONS

Medical Physics, vol. 11, No. 4, Jul./Aug. 1984, pp. 516–520, New York, US; A. E. Profio et al.: "Fluorometer for Endoscopic Diagnosis of Tumors".
Medical and Biological Engineering & Computing, vol. 25, No. 6, Nov. 1987, pp. 587–604, Stevanage, Herts, G. B., M. J. Martin et al.: "Fibre-optics and optical sensors in medicine", pp. 597, 601, paragraph 6.1
D. Lansing Taylor et al.: "Methods in Cell Biology", vol. 30, partie B, pp. 127–156, Academic Press, pp. 131–140.
IEEE Transactions on Biomedical Engineering, vol. BME-33, No. 2, Feb. 1986, pp. 117–132, J. L. Gehrich et al.: "Optical Fluorescence and Its Application to an Intravascular Blood Gas Monitoring System", p. 120, figure 6.

*Primary Examiner*—Angela D. Sykes
*Attorney, Agent, or Firm*—Oblon, Spivak, McClelland, Maier & Neustadt

[57] ABSTRACT

A device for measuring the pH of an appropriate target, without direct contact with the target, includes a light source for selecting a plurality of wavelengths for excitation of fluorescence of a fluorescent marker fixed to the target. The fluorescence emission spectrum is dependent on pH, the excitation wavelength being switched from one wavelength to another. Light is transmitted from the light source to the target, and the emitted fluorescence is collected, detected and read. The pH of the target is calculated from the ratio of the emitted fluorescence signals obtained successively at least at two excitation wavelengths.

16 Claims, 6 Drawing Sheets

DEVICE FOR MEASURING THE PH OF A TARGET, METHOD FOR USING SAID DEVICE AND APPLICATIONS THEREOF

BACKGROUND OF THE INVENTION

The subject of the present invention is a device for measuring the pH of an appropriate target, particularly a tumour, a method for using said device as well as its applications, particularly to the control of treatment of tumours by hyperthermy.

The early detection of tumours is essential for improving their prognosis; however, tumours of organs or of tissues are often difficult to detect and, in the case of cancer of the oesophagus, for example, the advent of oesophageal fibroscopy has not resulted in it being diagnosed at an earlier stage.

Other methods of early diagnosis have been proposed and involve a number of techniques:

1—fixation of a contrast agent or of a colouring agent and diagnosis by imaging; the colouring agent can either have a great affinity for nucleic acids (toluidine blue, for example) or, on the contrary, not have tumorous fixation (Lugol's solution, for example, which only reacts with glycogen of differentiated malpighian epithelium) or finally by the use of photosensitisers having a fluorescence peak during suitable light excitation (photodiagnosis). These techniques involve producing a fluorescence gradient between healthy tissue and tumorous tissue, which requires the elective fixation or the specific retention of the marker by the tumour; thus, these depend on many factors and especially on the vascularisation, the necrosis and the phagocytic capacity of the tumour.

2—the use of monoclonal antibodies or the vectorisation of the marker by liposomes; this technique, used on its own, has the disadvantage of requiring specific and expensive reagents.

3—the spectral study of the emitted fluorescence. This last method, which does not require the use of specific reagents, can avoid the abovementioned disadvantages.

It is possible to mention, as diagnostic methods using the spectral study of the emitted fluorescence:

the diagnostic method proposed by S. Andersson-Engels et al. (Lasers in Medical Science, 1988, 4, 171-181), which describes the localisation and detection of atheroma patches by measuring the self-fluorescence induced by a laser as the source of light excitation;

diagnosis of tumours by analysis of the fluorescence, which has especially been described in:

the article in the name of R. R. Alfano et al., which appeared in J. Quantum Electronics, 1984, Vol. OE-20, 12, 1507-1511, which describes measuring the self-fluorescence induced by a laser source, both on cancerous tissues and on healthy tissues, and which shows that the spectral profiles of cancerous tissues are different from those of healthy tissues.

and the methods by induced fluorescence, as specified in the article in the name of A. E. Profio et al., which appeared in Med. Phys., 1984, 11, 4, 516-520, which describes a fluorometer for the endoscopic diagnosis of tumours. More precisely, a fluorescent derivative of hematoporphyrin is injected and the tumour is then characterised by detecting the emitted fluorescence; the source of excitation is a purple light, conveyed through an optical fibre to the endoscope, whereas the emitted fluorescence as well as the reflected purple light are collected by another optical fibre. The fluorescence in red light and in purple light are separated using a dichroic mirror and a filter, and detected using photomultipliers. This method has the disadvantage that small tumours are difficult to localise, that it is entirely dependent on the measuring conditions, and that the concentration gradient between healthy and tumorous tissues is low with, moreover, a risk of cutaneous phototoxicity.

The methods for the diagnosis of tumours, by fluorescence, proposed in the prior art have, moreover, the major disadvantage of being absolute techniques, which result in many false positives or false negatives, because they are dependent on the measuring conditions (position of the collecting fibres, for example, or structure of the tissue to be studied).

A certain number of documents describe optrodes (optic electrodes) for measuring pH (Medical & Biological Engineering & Computing, 1987, 25, 5, 597-604; IEEE Transactions on Biomedical Engineering, 1986, BME-33, 117-132); however, such optrodes have the major disadvantage of not being able to be used in an imaging system, in so far as they only make possible limited measuring, at the point of contact with the tissue concerned.

SUMMARY OF THE INVENTION

The aim of the present invention is consequently to provide a device and a method which make it possible to solve the problem of detecting a tumour which is difficult to detect by the methods of the prior are or whose results are difficult to interpret, and also to solve the problem of dependence with respect to measuring conditions, encountered in the systems proposed in the prior art (A. E. Profio et al.); in effect, the solving of this problem is crucial for producing results which are reliable and make it possible to avoid false positives and false negatives.

The Inventors have, in order to do this, used measurements of the cell metabolism and, more particularly, the measurement of the intracellular pH using fluorescent markers having spectra which are dependent on the pH, as has been especially specified in J. A. Thomas et al., (Biochem., 1979, 18, 2210-2218), which describes the spectral characteristics of fluorescein and of 6-carboxyfluorescein (6-CF), which are dependent on the pH, for the purpose of detecting the possible presence of a tumour. Absorbance at 490 nm (peak) with reference to the absorbance at 465 nm (isobestic point, that is to say independent of the pH) shows that the absorbance is more significant at a pH of 7.8 than at a pH of 6.25.

The subject of the present invention is a device for measuring the pH of an appropriate target, without direct contact with said target, characterised in that it is comprised of:

a light source appropriate for selecting at least two wavelengths for excitation of the fluorescence of a fluorescent marker fixed to said target and whose fluorescence emission spectrum depends on the pH, which source is associated with a commutator or means for switching from one excitation wavelength to the other;

at least one transmission means from said light source to the target;

at least one means for collecting the emitted fluorescence;

a means for detecting and reading the emitted fluorescence; and a system for calculating the pH of the target from the ratio of the emitted fluorescence signals obtained successively at least at said two excitation wavelengths.

According to an advantageous embodiment of said device, the transmission means from the light source comprises at least one optical fibre.

According to another advantageous embodiment of said device, the means for collecting fluorescence comprises at least one optical fibre.

Optical fibre is understood to mean, in the meaning of the present invention, any fibre made of dielectric material intended to guide electromagnetic waves, for example visible or infrared.

In accordance with the invention, said transmission means and/or said collector means are associated with an endoscope, coupled to an image intensifier, itself connected to a video camera.

Endoscope is understood to mean, in the meaning of the present invention, both conventional endoscopes, that is to say devices intended for lighting and for making visible the inside of a cavity of the human body, and fibroscopes, that is to say flexible endoscopes formed from a bundle of extremely fine optical fibres.

According to an advantageous arrangement of the latter embodiment, said transmission means and/or said collector means are included in the endoscope.

Such a device makes it possible to obtain both a fluorescence image and a visible image of said target.

The means for measuring the fluorescence signals emitted by the marked target is advantageously a spectrophotometer and especially comprises at least one optical filter, at least one photomultiplier and/or at least one photodetector for converting said light signals, and a means for routing the corresponding electrical signals towards the system for calculating the pH.

Fluorescent markers sensitive to pH are more particularly described in the article which appeared in the name of R. Y. Tsien (Methods in Cell Biology, 1989, 30, 127–156), in which it is especially specified that the following fluorescent markers: fluorescein, fluorescein conjugated with dextran or with another inert molecule (DF), 5- and/or 6-carboxyfluorescein (CF), 2′,7′-bis(-carboxyethyl)-5- and/or 6-carboxyfluorescein (BCECF) and their esters, pyramine (8-hydroxypyrene-1,3,6-trisulphonate), 4-methylumbelliferone or 4-methyl-7-hydroxycoumarin (4-MU), 3,6-dicyanohydroquinone (DHPN), SNARF-1 and SNAF-2 (respectively semi-naphthorhodofluor and semi-naphthofluorescein), exhibit a pair of wavelengths whose excitation ratio increases with pH.

These markers especially make it possible measure the pH of cytosol.

In accordance with the invention, the fluorescent marker is advantageously associated with appropriate liposomes and/or monoclonal antibodies.

According to another embodiment of the device in accordance with the invention, the system for calculating the pH advantageously comprises a means for calculating the ratio of the emitted fluorescence signals, obtained successively at least at said two excitation wavelengths, and a means for reading the pH corresponding to the ratio obtained on a calibration curve of said marker as a function of the pH.

According to an advantageous arrangement of this embodiment, said calculating system also comprises a system for controlling the switching means.

Such a system is especially represented by an appropriate microcomputer which makes it possible both obtain the pH, as a function of the ratios of the emitted fluorescence signals, and to control the means for switching from one excitation wavelength to another.

When the target is a cell, a tissue or an organ, the device in accordance with the invention has the following advantages:

measuring of the pH is carried out in situ without direct contact with said cell, tissue or organ;

this pH measurement makes it possible to detect a tumour, because the tumorous cells have a more acidic pH than normal cells, in so far as the tumorous cells are generally anoxic and thus have recourse to anaerobic glycolysis, with the consequent production of lactic acid;

this pH measurement is reliable, because it uses a ratio of fluorescence intensities at two different wavelengths, which avoids dependence with respect to measuring parameters (especially structure of the target and angle between the collector fibre and the fluorescence emitted by the target), often significant in fluorescence measurements, and which makes it possible to obtain good-quality signals and optionally to amplify them.

Another subject of the present invention is a device for controlling hyperthermy in the treatment of tumours by hyperthermy, characterised in that it comprises a device for measuring the pH in accordance with the invention, associated with an appropriate means for heating said tumour.

Said heating means is advantageously chosen from any one of the following means: laser source, microwaves, ultrasound, radio frequency or hot water circuit.

In accordance with the invention, said heating means is especially associated with a means for focusing the heat produced towards the tumour, especially a probe, a catheter or an external antenna.

Another subject of the present invention is a method for using the device in accordance with the invention which makes it possible to obtain data characteristic of the development over time of the pH of an appropriate target, characterised in that it comprises:

bringing the target to be analysed into contact with a fluorescent marker having at least two excitation peaks and an emission peak and whose emission spectrum is dependent on the pH;

successively exciting the target thus treated at said excitation wavelengths of said fluorescent marker;

successively measuring the fluorescence emitted by said target to be analysed at said excitation wavelengths; and calculating the pH of said target to be analysed from the ratio of the emitted fluorescence signals, obtained successively at least at said two excitation wavelengths, by reading the pH corresponding to the ratio obtained on a calibration curve of said marker as a function of the pH.

According to an advantageous embodiment of said method, prior to bringing the target to be analysed into contact with the fluorescent marker, said target is brought into contact with a sugar, especially glucose.

Bringing the target into contact with the sugar makes the method even more sensitive, in so far as it makes it possible to further reduce the pH of the tumorous tissues with respect to the healthy tissues and thus to increase the difference between tumorous tissue and healthy tissue.

According to an advantageous embodiment of said process, the fluorescent marker is especially chosen from the group which comprises fluorescein, fluorescein conjugated with dextran or with another inert molecule (DF), 5- and/or 6-carboxyfluorescein (CF), 2',7'-bis (carboxyethyl) -5- and/or 6-carboxyfluorescein (BCECF) and their esters, pyramine (8-hydroxypyrene-1,3,6-trisulphonate), 4-methylumbelliferone or 4-methyl-7-hydroxycoumarin (4-MU), 3,6-dicyanohydroquinone (DHPN), SNARF-1 and SNAF-2 (respectively semi-naphthorhodofluor and semi-naphthofluorescein).

According to an advantageous arrangement of this embodiment, said fluorescent marker is associated with appropriate liposomes and/or monoclonal antibodies.

The devices and the method in accordance with the invention are applied particularly advantageously to measuring the pH of tumours, especially accessible only endoscopically, and make it possible to monitor the pH of the tumour at different points and the development of the treatment by hyperthermy of said tumours, which makes it possible to calculate the useful thermal dose at any point of the tumour; in effect, the thermal dose to be applied is different according to the pH.

The device in accordance with the invention also makes it possible to control, in real time, the thermal dose to be applied.

BRIEF DESCRIPTION OF THE DRAWINGS

Besides the above arrangements, the invention further comprises other arrangements, which will emerge from the description which will follow, which refers to examples of the use of the method in accordance with the invention and to a detailed description of the device according to the invention, with reference to the appended drawings, in which.

However, it must be well understood that these examples are given solely by way of illustration of the subject of the invention, of which they constitute in no way a limitation.

DETAILED DESCRIPTION OF THE DRAWINGS

Figure 1:
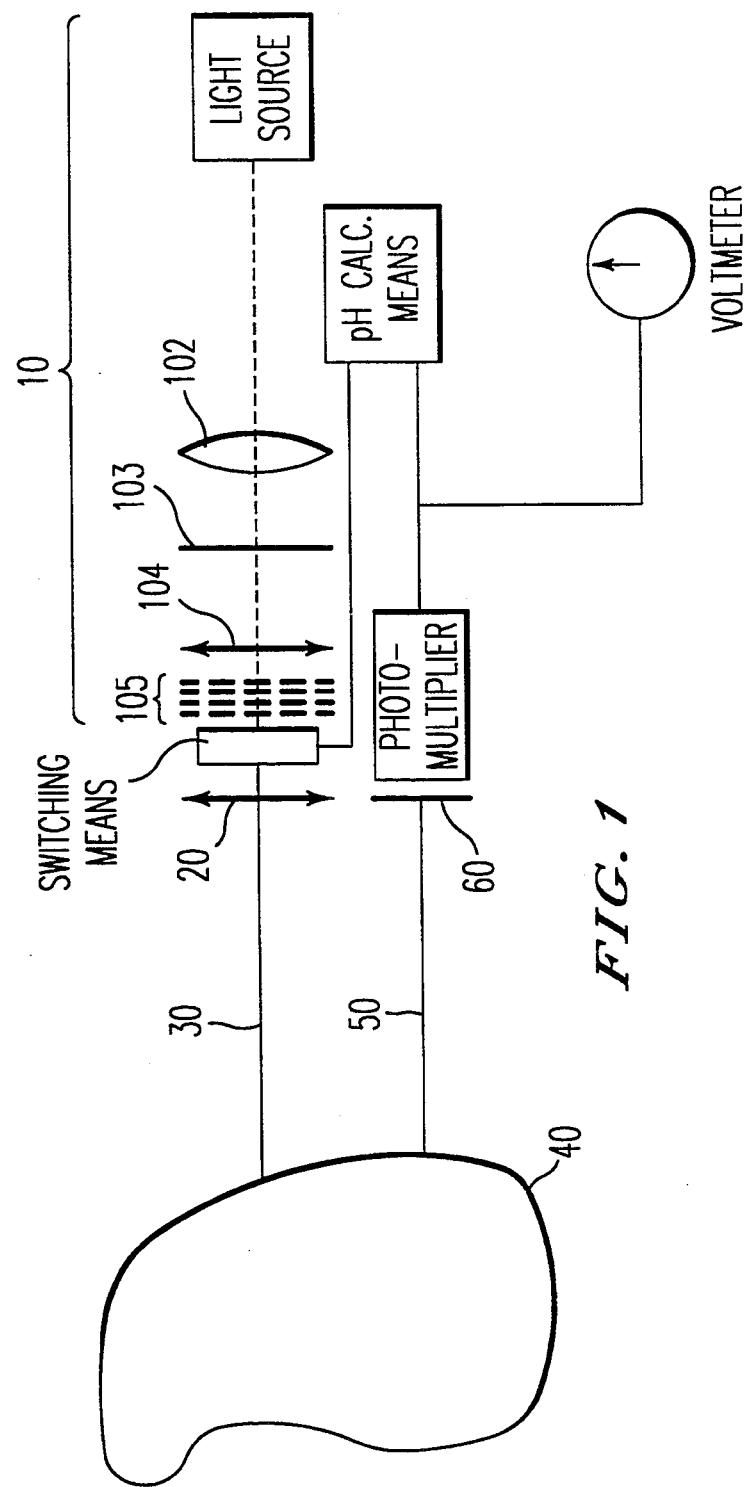
FIGS. 1 and 2 represent diagrammatically two embodiments of a device for measuring the pH in accordance with the invention.

FIG. 1 represents a diagrammatic view of a device for measuring pH in accordance with the invention, comprising:

a source of excitation 10 which, in the implementation represented, and in a non-limiting way, comprises a Ushio 155 Xenon arc lamp (Ushio, Japan) 101, a spherical mirror with a radius of curvature of 3 cm 102, a 66061 Oriel 103 condenser (Oriel, USA), a converging lens with a diameter of 7.5 cm and a focal length of 200 mm 104, and interference filters 105 centred on 450 nm, 465 nm, 490 nm and 500 nm, making it possible to select the desired wavelengths; a switching means 106 or commutator means makes it possible to switch from one excitation wavelength to another; a final lens 20, with a diameter of 22.4 mm, makes it possible to focus the light on the heart of a 600 $\mu$m transmission fibre 30 (N.A.=0.48). The power delivered is 3 mW on a strip of 10 nm. The transmission fibre is in contact with the target 40, especially a tissue, the pH of which is to be analysed in situ:

a collector fibre 50, with a diameter of 600 $\mu$m, is connected to a MC1-03 monochromator (Optometrics, USA) 60 connected to a photomultiplier 70 (Mini-Chrom; 300 nm to 800 nm band);

reading of the signal is carried out, in the implementation represented, on a Dipitol 80 voltmeter;

the calculating system is represented by a microcomputer 90, to which are connected the collector system (collector fibre 50, monochromator 60 and photomultiplier 70) and the switching means 106.

The calculating system makes it possible to calculate the ratio of the emitted fluorescence signals obtained at two appropriate excitation wavelengths at the marker used, and then to calculate the pH of the target 40 corresponding to the ratio obtained on a calibration curve of said marker as a function of the pH.

Figure 2:
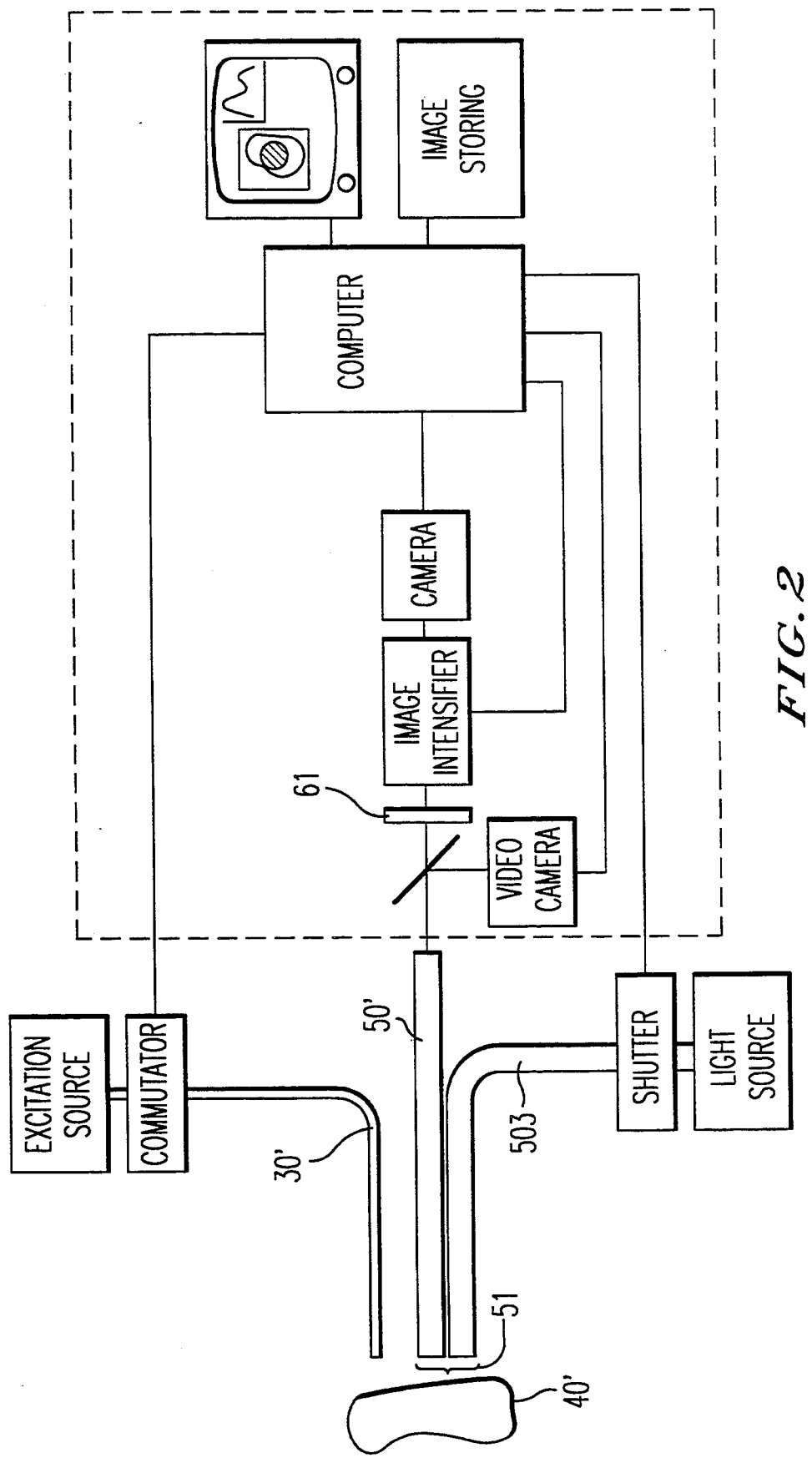

FIG. 2 represents the diagrammatic view of a device for measuring pH in accordance with the invention, in which the collector fibre 50' is included in an endoscope 51 which thus makes it possible to obtain both a fluorescence image and an image in the visible region.

The device represented in FIG. 2 comprises:

a fluorescence excitation source 10', the characteristics of which can be identical to that of the source described in Example 1, which is associated with an excitation wavelength commutator 106', which can advantageously be controlled by a computer 901; the commutator 106' is connected to the target 40' via a transmission fibre 30' of the same type as that in Example 1;

an endoscope 51, which comprises a light source 501, a shutter 502 and a bundle of appropriate fibres 503;

a collector fibre 50', which is enclosed in an endoscope 51, is associated with a filter 61 for selecting the emission wavelength (515 nm, when the marker is 6-CF, for example) or with a monochromator; it is coupled, on the one hand, to an image intensifier 52, itself connected to a camera 53, and, on the other hand, to a video camera 54 which makes it possible to obtain an image of the target.

The fluorescence signals (fluorescence image) and the image in the visible region are directed towards the microcomputer 901.

The collector system (collector fibre 50', filter 61 or monochromator, image intensifier 52, camera 53), the endoscope 51, the video camera 54 and the computer 901 constitute an imaging system which makes it possible to store both fluorescence spectra and images.

The devices according to the invention make it possible to measure the pH of a target.

The procedure is as follows: the measurement is carried out on CDF mice carrying a P388 lymphoid leukaemia.

The tumour is grafted subcutaneously on one side of the mouse.

The spontaneous development of the tumour is reproducible: a tumour with a diameter of 20 mm is obtained 12 days after grafting.

An intraperitoneal injection of 250 μl of 5,6-CF in a 0.9% NaCl buffer at a concentration of $10^{-3}$M, $5 \times 10^{-3}$M or $10^{-4}$M (5 mg/kg, 2.5 mg/kg or 0.5 mg/kg) is carried out on day 12.

Before measuring the fluorescence and calculating the pH of the tumour, the tumorous region and a corresponding healthy tissue are shaved.

Injection of 5,6-CF being regarded as time zero, the fluorescence intensities are measured at times $-3$ minutes, $+3$ minutes, and then every 10 minutes, for 1 hour.

Controlled tests are carried out on normal skin and on tumours which have not been brought into contact with the fluorescent marker.

Figure 3:
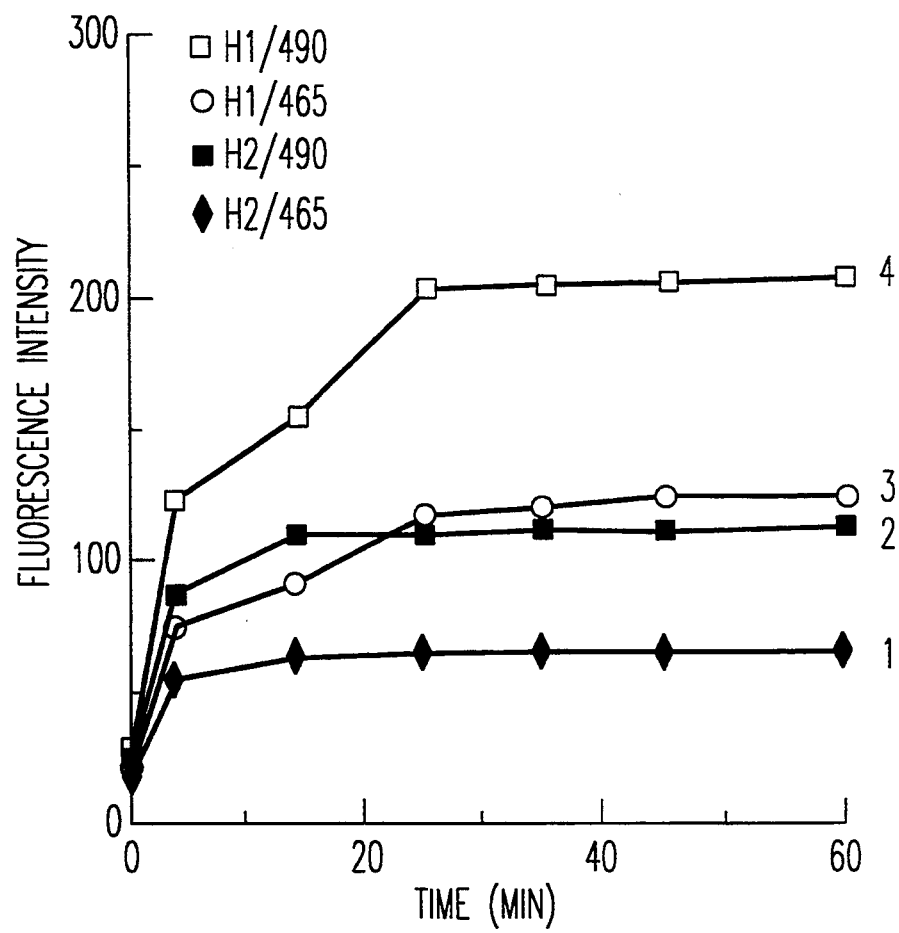
FIG. 3 represents the kinetic fluorescence profile of two healthy targets ($H_1$ and $H_2$)

FIG. 3, which comprises, in the abscissa, the time in minutes and, in the ordinate, the fluorescence intensities, shows the various kinetic profiles between two healthy tissue regions (H1 and H2). The maximum fluorescence intensities can be relatively different; the maximum intensities are reached in 5 to 30 minutes, but are different for each tissue. The differences in the kinetic profiles can be due especially to disturbances in the detection conditions in the two regions. Curves 1 and 2 show the kinetic profiles of the tissue H2, at 465 and 490 nm respectively, and curves 3 and 4 show the kinetic profiles of the tissue H1, at 465 and 490 nm respectively.

Figure 4:
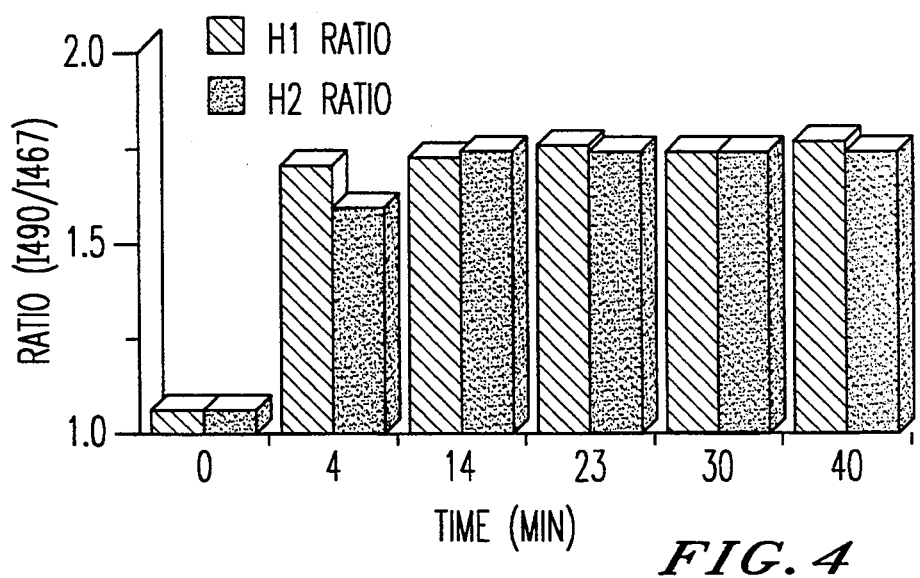
FIG. 4 represents the effect of 5,6-CF on the values of the ratio of emission fluorescence intensities of two healthy regions of the skin, calculated from the fluorescence intensities obtained at 490 and 465 nm.

FIG. 4 shows that whatever the fluorescence intensities in the two regions, the differences do not affect the values of the ratios, which remain constant and are virtually identical for the two regions H1 and H2 between 15 min and 50 min after the injection.

Figure 5:
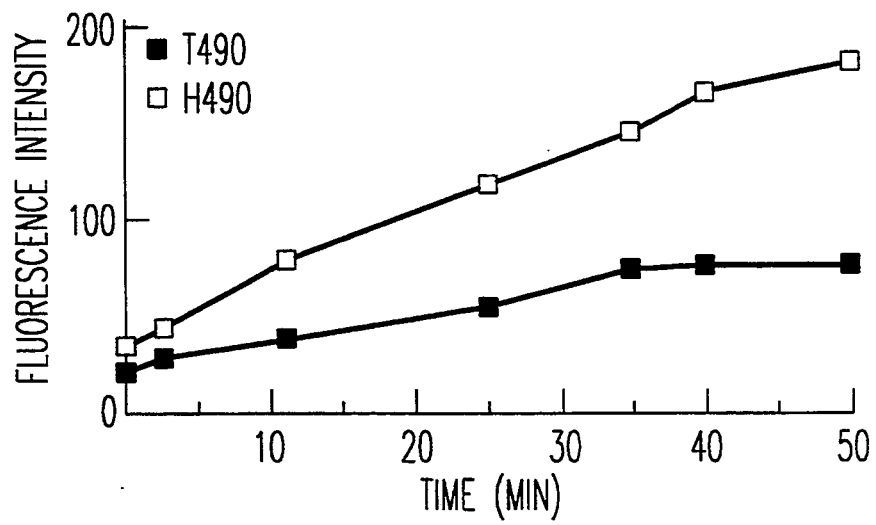
FIG. 5 represents the kinetic fluorescence profile of normal and tumorous tissues after an injection of 250 $\mu$l of $10^{-3}$M 5,6-CF.

FIG. 5 shows the fluorescence intensities obtained as a function of time, on a healthy tissue (-□-) and on a tumorous tissue (-■-). This figure gives the kinetic profiles obtained after injection of $10^{-3}$M CF. The fluorescence of the normal tissues is greater than that of the tumorous tissues.

Figure 6:
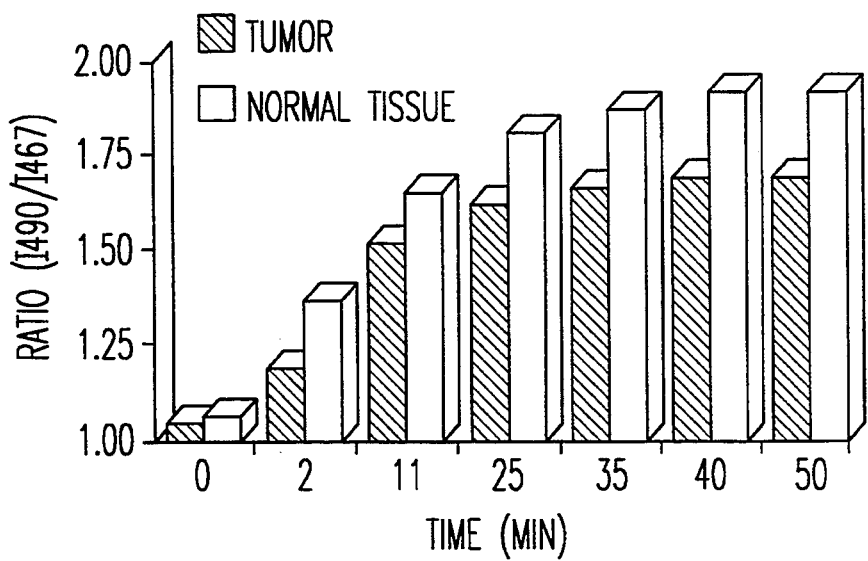
FIG. 6 represents the effect of a healthy tissue or of a tumorous tissue on the values of the ratios of fluorescence intensities, calculated from the intensities obtained at 490 and 465 nm.

FIG. 6 shows the values of the I490/I465 ratios and shows that there indeed exists a significant difference between the healthy tissues and the tumorous tissues.

Figure 7:
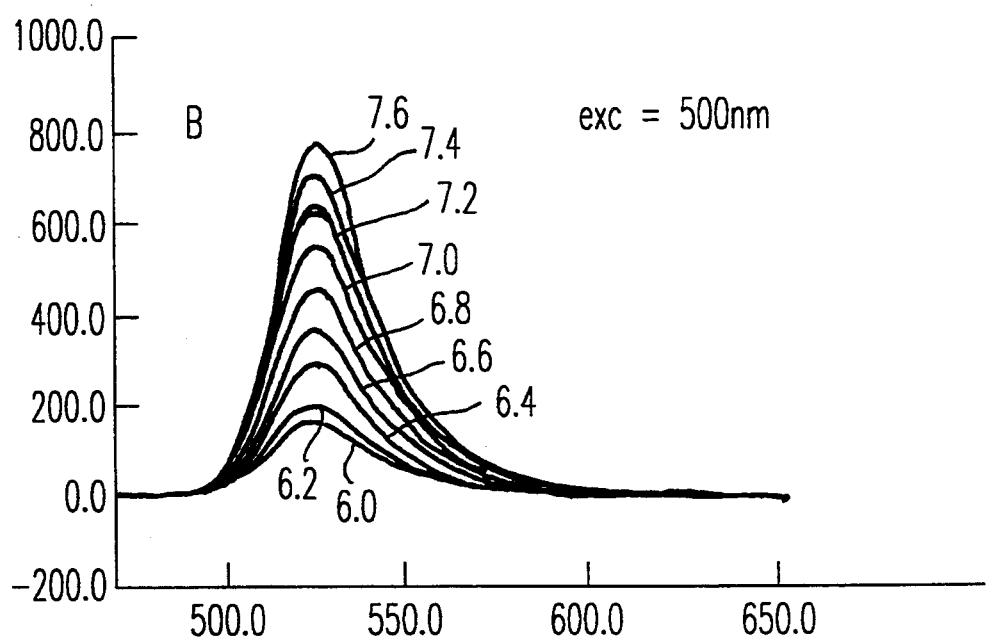
FIG. 7 represents the development of the fluorescence emission spectrum of 5,6-CF as a function of the pH.
Figure 8:
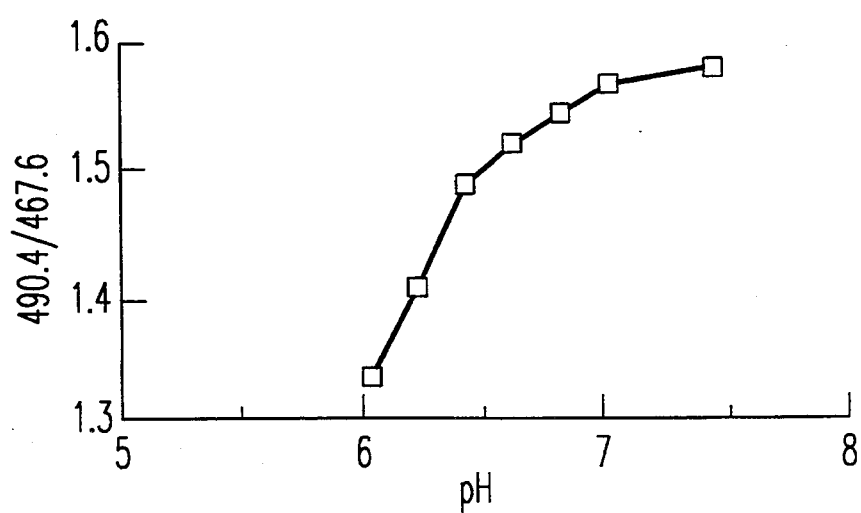
FIG. 8 represents the calibration curve of 6-CF as a function of the pH.

The results show that penetration of the excitation light is sufficient to detect spectral fluorescence variations by the ratios method and make it possible to obtain the value of the pH at the tumour; in effect, FIG. 7 shows the development of the fluorescence emission spectrum of carboxyfluorescein as a function of the pH and FIG. 8 shows the calibration curve of 5,6-CF as a function of the pH.

The process in accordance with the invention also makes it possible to evaluate the thermal dose (duration and time) necessary to destroy tumorous cells as a function of the pH of said cells.

Figure 9:
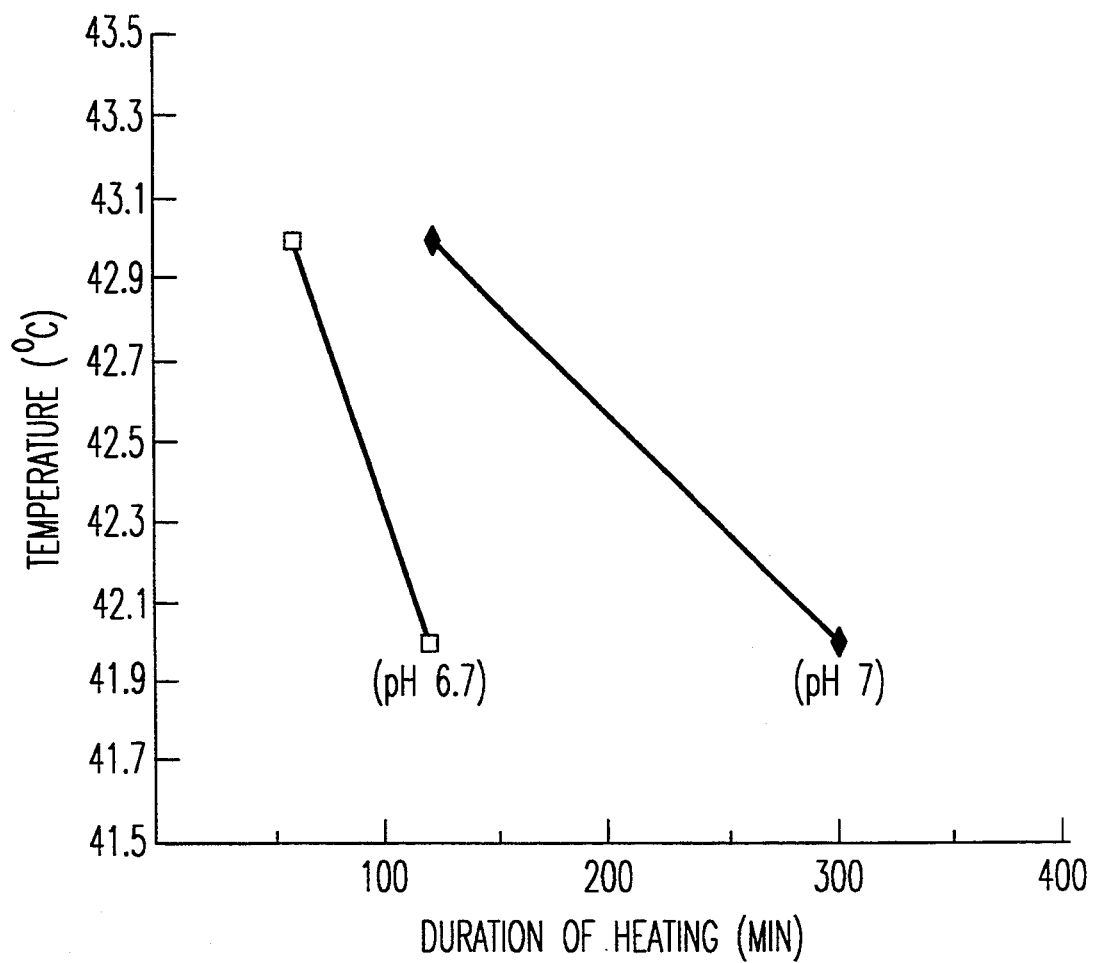
FIG. 9 shows the influence of the pH on a treatment by hyperthermy.

FIG. 9 shows the influence of the pH on the resistance of cell cultures subjected to a hyperthermy.

As well as that emerging from the above, the invention is in no way limited to those of its modes of use, implementation and of application which have just been described mre explicitly; on the contrary, it embraces all the variants thereof which can come to the mind of the technical export in the matter without departing from the scope nor from the context of the present invention.

We claim:

1. A device for measuring the pH of an appropriate target without direct contact with said target, consisting essentially of:
    a light source (101) which can emit a plurality of wavelengths of light of which two wavelengths are selected for excitation of a fluorescent marker fixed to said target, the fluorescent marker emitting fluorescent radiation upon excitation, the emission spectrum of which depends on the pH, of the environment of the marker in the target and said source being associated with a means for switching (106, 106') from one excitation wavelength to the other;
    at least one transmission means (30, 30') extending from said light source to the target (40, 40');
    at least one means for collecting (50, 50') the fluorescence emitted from the fluorescent marker;
    a means for detecting and reading the emitted fluorescence (60, 70, 80; 61, 52, 53) from the collecting means; and
    a means for calculating the pH of the target from the ratio of the emitted fluorescence signals, obtained successively at said two excitation wavelengths (90, 901).

2. The device according to claim 1, wherein the transmission means from the light source comprises at least one optical fiber.

3. The device according to claim 1, wherein the means for collecting fluorescence comprises at least one optical fiber.

4. The device according to claim 1, 2 or 3, wherein said transmission means, said collector means or both are associated with an endoscope (51) coupled to an image intensifier (52) which itself is connected to a video camera (53).

5. The device according to claim 4, wherein said transmission means, said collector means or both are enclosed in the endoscope.

6. The device according to claim 1, 2 or 3, wherein the fluorescent marker is associated with appropriate liposomes, monoclonal antibodies, or both.

7. The device according to claim 1, 2 or 3, wherein the said pH is calculated by a system which comprises a means for calculating the ratio of the emitted fluorescence signals obtained successively at said two excitation wavelengths, and a means for reading the pH corresponding to the ratio obtained on a calibration curve of said marker as a function of the pH.

8. The device according to claim 7, wherein the calculating system further comprises a system for controlling the switching means.

9. A device for controlling hyperthermy in the treatment of tumours by hyperthermy, comprising a device for measuring pH according to claim 1 associated with an appropriate means for heating said tumour.

10. The device according to claim 9, wherein said heating means is associated with a means for focusing the heat produced, a catheter or an external antenna.

11. The device according to claim 10, wherein said means for focusing heat is a probe.

12. A method of obtaining the data characteristic of the development over time of the pH of an appropriate target employing the device of claim 1, comprising:
    bringing the target to be analyzed into contact with a fluorescent marker having at least two excitation peaks and an emission peak and whose emission spectrum is dependent on the pH;

successively exciting the target thus treated at said excitation wavelengths of said fluorescent marker;

successively measuring the fluorescence emitted by said target to be analyzed at said excitation wavelengths; and calculating the pH of said target to be analyzed from the ratio of the emitted fluorescence signals, obtained successively at least at said two excitation wavelengths, by reading the pH corresponding to the ratio obtained on a calibration curve of said marker as a function of the pH.

13. The method according to claim 12, wherein, prior to bringing the target to be analyzed into contact with the fluorescent marker, said target is brought into contact with a sugar.

14. The method according to claim 3, wherein said sugar is glucose.

15. The method according to claim 12 or 13, wherein the fluorescent marker is selected from the group consisting of fluorescein, fluorescein conjugated with dextran or another inert molecule (DF), 5- and/or 6-carboxyfluorescein (CF), 2',7'-bis(carboxyethyl)-5- and/or 6-carboxyfluorescein (BCECF) and their esters, pyramine (8-hydroxypyrene-1,3,6-trisulfonate), 4-methylumbelliferone or 4-methyl-7-hydroxycoumarin (4-MU), 3,6-dicyanohydroquinone (DHPN), SNARF-1 and SNAF-2 which are respectively semi-naphthorhodofluor and semi-naphthofluorescein.

16. The method of claim 15, wherein said fluorescent marker is associated with liposomes, monoclonal antibodies, or both.

* * * * *